（12） United States Patent
Narayan et al.

(10) Patent No.: US 9,322,713 B2
(45) Date of Patent: Apr. 26, 2016

(54) ARTIFICIAL RETINA DEVICE

(75) Inventors: Kavassery Sureswaran Narayan, Bangalore (IN); Vini Gautam, New Delhi (IN); Monojit Bag, Bangalore (IN)

(73) Assignee: JAWAHARLAL NEHRU CENTRE FOR ADVANCED SCIENTIFIC RESEARCH, Bangalore (IN)

( * ) Notice: Subject to any disclaimer, the term of this patent is extended or adjusted under 35 U.S.C. 154(b) by 0 days.

(21) Appl. No.: 14/235,603

(22) PCT Filed: Jul. 20, 2012

(86) PCT No.: PCT/IB2012/053711
§ 371 (c)(1),
(2), (4) Date: Jan. 28, 2014

(87) PCT Pub. No.: WO2013/030687
PCT Pub. Date: Mar. 7, 2013

(65) Prior Publication Data
US 2014/0176950 A1    Jun. 26, 2014

(30) Foreign Application Priority Data
Aug. 30, 2011 (IN) .......................... 2997/CHE/2011

(51) Int. Cl.
*G01J 3/50* (2006.01)
*H01L 51/42* (2006.01)
*A61N 1/05* (2006.01)
(Continued)

(52) U.S. Cl.
CPC .................. *G01J 3/50* (2013.01); *A61N 1/0543* (2013.01); *H01L 51/4253* (2013.01); *A61N 1/36046* (2013.01); *G01J 2003/466* (2013.01); *Y02E 10/549* (2013.01)

(58) Field of Classification Search
USPC .......................................... 257/184; 356/407
See application file for complete search history.

(56) References Cited

U.S. PATENT DOCUMENTS 4,870,268 A    9/1989    Vincent et al.
5,424,974 A    6/1995    Liu et al.
5,965,875 A    10/1999   Merrill
(Continued)

FOREIGN PATENT DOCUMENTS

CN    101149559 A    3/2008
EP    1 207 556      5/2002
(Continued)

OTHER PUBLICATIONS

Gautam et al., Dynamics of Bulk Polymer Heterostructure/Electrolyte Devices, Physical Chemistry Letters, 2010, pp. 3277-3282.*
(Continued)

*Primary Examiner* — Zandra Smith
*Assistant Examiner* — Lawrence Tynes, Jr.
(74) *Attorney, Agent, or Firm* — Foley & Lardner LLP

(57) ABSTRACT

The present technology provides a color-sensing device that includes an electrically-conductive substrate and a bulk heterojunction (BHJ) polymer layer formed on the substrate. The color-sensing device is configured to detect a first color of two colors and produce a first electrical signal that includes a first current response indicating detection of the first color. The color-sensing device is further configured to detect a second color of the two colors and produce a second electrical signal that includes a second current response indicating detection of the second color.

20 Claims, 10 Drawing Sheets

(51) Int. Cl.
*G01J 3/46* (2006.01)
*A61N 1/36* (2006.01)

(56) References Cited

U.S. PATENT DOCUMENTS

| | | | |
|---|---|---|---|
| 6,324,429 | B1 | 11/2001 | Shire et al. |
| 6,611,716 | B2 | 8/2003 | Chow et al. |
| 7,003,354 | B2 | 2/2006 | Chow et al. |
| 7,031,776 | B2 | 4/2006 | Chow et al. |
| 7,079,900 | B2 | 7/2006 | Greenburg et al. |
| 7,139,612 | B2 | 11/2006 | Chow et al. |
| 7,272,447 | B2 | 9/2007 | Stett et al. |
| 7,774,931 | B2 | 8/2010 | Tai et al. |
| 2003/0097165 | A1 | 5/2003 | Krulevitch et al. |
| 2003/0097166 | A1 | 5/2003 | Krulevitch et al. |
| 2004/0267344 | A1 | 12/2004 | Stett et al. |
| 2006/0118722 | A1* | 6/2006 | Pham ..................... 250/338.4 |
| 2007/0095669 | A1 | 5/2007 | Lau et al. |
| 2007/0142878 | A1 | 6/2007 | Krulevitch et al. |
| 2008/0288067 | A1 | 11/2008 | Flood |
| 2009/0001278 | A1* | 1/2009 | Jones et al. ............. 250/370.13 |
| 2009/0210055 | A1 | 8/2009 | Chang et al. |
| 2009/0292325 | A1 | 11/2009 | Cederna et al. |
| 2010/0155707 | A1 | 6/2010 | Anthopoulos |
| 2010/0243863 | A1* | 9/2010 | Higuchi et al. ............... 250/206 |

FOREIGN PATENT DOCUMENTS

| | | |
|---|---|---|
| WO | WO-2008/122778 | 10/2008 |
| WO | WO-2008/141271 | 11/2008 |
| WO | WO-2009/143625 | 12/2009 |

OTHER PUBLICATIONS

Kim et al., A strong regioregularity effect in self-organizing conjugated polymer films and high-efficiency polythiophene:fullerene solar cells, Nature Materials, vol. 5, Mar. 2006, pp. 197-203.*
Hapip et al., Influence of poly(3-alkylthiophene) (P3ATs) structure on P3AT/ Gaq3 films for organic solar celis, materials and research, vol. 15, p. 2.*
Gautam et al., Dynamics of Bulk Polymer Heterostructure/Electrolyte Devices, The Journal of Physical Chemistry Letters, 3277-3282.*
Ahuja, A.K. et al., "An In Vitro Model of a Retinal Prosthesis," IEEE Transactions on Biomedical Engineering, Jun. 2008, vol. 55, No. 6, pp. 1744-1753.
Ahuja, A.K. et al., "The Dependence of Spectral Impedance on Disc Microelectrode Radius," IEEE Transactions on Biomedical Engineering, Apr. 2008, vol. 55, No. 4, pp. 1457-1460.
Antognazza, M. R. et al., "A hybrid solid-liquid polymer photodiode for the bioenvironment," Appl. Phys. Lett., vol. 94, 2009, pp. 243501-1-243501-3.
Antognazza, M. R. et al., "Organic-based tristimuli colorimeter," Appl. Phys. lett., 2007, vol. 90, pp. 163509-1-163509-3.
Arun, N. et al., "Conducting Polymers as Antennas for Probing Biophysical Activities," J. Phys. Chem. B, vol. 112, 2008, pp. 1564-1569.
Asplund, M. L. M., et al., "Neural Microcontacts with Wire Electrodes and Woven Logic," Materials Research Society Spring Meeting, 2007, downloaded from http://www.mrs.org/smrs/doc.asp?CID=8697&DID=193935, 1 pp.
Basinger, B. C., et al., "Finite element modeling of retinal prosthesis mechanics," Journal of Neural Engineering, 2009, vol. 6, No. 5, 9 pp.
Behrend, M. et al., "Selective Labeling of Retinal Ganglion Cells with Calcium Indicators by Retrograde Loading In Virto," Journal of Neuroscience Methods, 2009, vol. 179, pp. 166-172.
Behrend, M.R. et al., "Dynamic Current Density of the Disk Electrode Double-Layer," IEEE Transactions on Biomedical Engineering, Mar. 2008, vol. 55, No. 3, pp. 1056-1062.
Bharath A., et al., "Next Generation Artificial Vision Systems Reverse Engineering the Human Visual System," 2008, Artech House, Inc., Ch. 10.4.2 to 10.5, Fig 10.8, pp. 264 and 271-288.

Blau, A. et al., "Prototyping all-polymer bioelectrical signal transducers," IFMBE Proceedings, vol. 25, 2009, pp. 327-330.
Caspi, A. et al., "Feasibility Study of a Retinal Prosthesis: Spatial Vision with a 16-Electrode Implant," Arch Ophthalmol, Apr. 2009, vol. 127, No. 4, pp. 398-401.
Chow, A. Y. et al., "Implantation of Silicon Chip Microphotodiode Arrays into the Cat Subretinal Space," IEEE Transactions on Neural Systems and Rehabilitation Engineering, vol. 9, No. 1, Mar. 2001, pp. 86-95.
Colodetti, L. et al., "Pathology of Damaging Electrical Stimulation in the Retina," Experimental Eye Research, 2007, 85, pp. 23-33.
De Balthasar, C. et al., "Factors Affecting Perceptual Thresholds in Epiretinal Prostheses," Investigative Ophthalmology and Visual Science, Jun. 2008, vol. 49, No. 6, pp. 2303-2314.
De Paoli, M. A. et al., "Electrochemistry, Polymers and Opto-Electronic Devices: A Combination with a Future," J. Braz. Chem. Soc., vol. 13, No. 4, 2002, pp. 410-424.
Gao, J. et al., "Polymer p-i-n Junction Photovoltaic Cells," Adv. Mater., vol. 10, No. 9, 1998, pp. 692-695.
Ghezzi, D., et al., "A hybrid bioorganic interface for neuronal photoactivation," Nature Communications 2011, vol. 21, No. 166, pp. 1-7.
Green, R. A. et al., "Conducting polymers for neural interfaces: Challenges in developing an effective long-term implant," 2008, vol. 29, pp. 3393-3399.
Greenbaum, E. et al., "Metabolic Prosthesis for Oxygenation of Ischemic Tissue," IEEE Transactions on Biomedical Engineering, Feb. 2009, vol. 56, No. 2, pp. 528-531.
Greenwald, S.H. et al., "Brightness as a Function of Current Amplitude in Human Retinal Electrical Stimulation," Investigative Ophthalmology & Visual science, Nov. 2009, vol. 50, No. 11, pp. 5017-5025.
Gupta, D. et al., "Transport of Photogenerated Charge Carriers in Polymer Semiconductors," Proceedings of the IEEE, vol. 97, No. 9, Sep. 2009, pp. 1558-1569.
Gurunathan, K. et al., "Review: Electrochemically synthesised conducting polymeric materials for applications towards technology in electronics, optoelectronics and energy storage devices," Materials Chemistry and Physics, 1999, vol. 61, pp. 173-191.
Guven, D. et al., "Implantation of an Inactive Epiretinal Poly (Dimethyl Siloxane) Electrode Array in Dogs," Experimental Eye Research, 2006, vol. 82, pp. 81-90.
Guven, D., et al., "Long-term stimulation by active epiretinal implants in normal and RCD1 dogs," Journal of Neural Engineering, 2005, vol. 2, No. 1, pp. S65-S73.
Horsager, A. et al., "Predicting Visual Sensitivity in Retinal Prosthesis Patients," Investigative Ophthalmology and Visual Science, Apr. 2009, vol. 50, No. 4, pp. 1483-1491.
International Search Report and Written Opinion for PCT/IB2010/002170 mailed Jan. 14, 2011.
International Search Report and Written Opinion received for PCT/IB2012/053711 dated Oct. 2, 2012.
Kabra, D. et al., "Charge carrier dynamics in organic semiconductors by position dependent optical probing," J. Appl. Phys., vol. 101, 2007, pp. 064510-1-064510-7.
Kabra, D. et al., "Model for Studies of Lateral Photovoltaic Effect in Polymeric Semiconductors," IEEE Sensors Journal, vol. 8, No. 10, Oct. 2008, pp. 1663-1671.
Kendir, G.A. et al., "An Optimal Design Methodology for Inductive Power Link with Class-E Amplifier," IEEE Transactions on Circuits and Systems—I: Regular Papers, May 2005, vol. 52, No. 5, pp. 857-866.
Kim, J. et al., "A Fully Integrated DPSK Demodulator for High Density Biomedical Implants," Proceedings of Biomedical Circuits and Systems Conference, 2008, pp. 93-96.
Lawrence Livermore National Laboratory, "Using Micro-Fabrication Methods to Further Develop Biocompatible Microelectrode Array for Artificial Retina Device," Feb. 4, 2012, 3 pages, retrieved from: http://www.azonano.com/news.aspx?newsID=15783 on Feb. 5, 2013.
Lazzi, G., "Thermal Effects of Bioimplants: Power Dissipation Characteristics and Computational Methods," IEEE Engineering in Medicine and Biology Magazine, Sep./Oct. 2005, pp. 75-81.

(56) References Cited

OTHER PUBLICATIONS

Mahadevappa, M. et al., "Perceptual Thresholds and Electrode Impedance in Three Retinal Prosthesis Subjects," IEEE Transactions on Neural Systems and Rehabilitation Engineering, Jun. 2005, vol. 12, No. 2, pp. 201-206.
Meixner, R. M. et al., "Wavelength-selective organic field-effect phototransistors based on dye-doped poly-3-hexylthiophene," Appl. Phys. Lett., 2007, vol. 89, pp. 092110-1-092110-3.
Non-final Office Action received for U.S. Appl. No. 13/124,357 dated Feb. 12, 2013.
Non-final Office Action received for U.S. Appl. No. 13/124,357 dated Dec. 3, 2013.
Final Office Action received for U.S. Appl. No. 13/124,357 dated May 14, 2013.
Nyberg, T. et al., "Ion conducting polymer microelectrodes for interfacing with neural networks," Journal of Neuroscience Methods, vol. 160, 2007, pp. 16-25.
Optobionics webpage, "ASR Device," (http://www.optobionics.com/asrdevice.shtml), printed Jun. 23, 2010, 1 page.
Pennisi, C. P. et al., "Spatial Distribution of the Electric Potential from Photosystem I Reaction Centers in Lipid Vesicles," IEEE Transactions on Nanobioscience, Jun. 2008, vol. 7, No. 2, pp. 164-171.
Pennisi, C.P. et al., "Incorporation of Photosynthetic Reaction Centers in the Membrane of Human Cells: Toward a New Tool for Optical Control of Cell Activity," Cellular and Molecular Bioengineering, Mar. 2009, vol. 2, No. 1, pp. 156-165.
Rao, M. et al., "Studies of Photogenerated Charge Carriers from Donor-Acceptor Interfaces in Organic Field Effect Transistors. Implications for Organic Solar Cells," 2010, J. Phys. Chem. C, vol. 114, No. 48, pp. 20609-20613.
Ray, A. et al., "Immunocytochemical Analysis of Retinal Neurons under Electrical Stimulation," Brain Research, Feb. 19, 2009, vol. 1255, pp. 89-97.
RLE Progress Report, "Chapter 17. The Retinal Implant Project," retrieved from the Internet<URL:http://www.rle.mit.edu/rleonline/ProgressReports/2104_17.pdf>, 12 pages.
Rodger, D.C. et al., "Flexible Parylene-Based Multielectrode Array Technology for High-Density Neural Stimulation and Recording," Sensors and Actuators B: Chemical, 2008, vol. 132, pp. 449-460.
Roizenblatt, R. et al., "Nanobiolistic Delivery of Indicators to the Living Mouse Retina," Journal of Neuroscience Methods, 2006, vol. 153, pp. 154-161.
Sanders, C. et al., "Dynamic Interactions of Retinal Prosthesis Electrodes with Neural Tissue and Materials Science in Electrode Design," Artificial Sight, 2008, pp. 209-226.
Second Sight Medical Products, Inc. webpage, About Us, retrieved from the internet: <URL:http://www.2-sight.com>, printed Jun. 23, 2010, 1 page.
Seo, J. et al., "Biocompatibility of polyimide microelectrode array for retinal stimulation," Materials Science and Engineering C, vol. 24, 2004, pp. 185-189.
Shah, S. et al., "Electrical Properties of Retinal-Electrode Interface," Journal of Neural Engineering, 2007, vol. 4, pp. S24-S29.
Simon, J., Molecular Solar Cells. Part 1: Devices based on Easily Doped Insulators, International Journal of Applied Chemistry, vol. 3, No. 3, 2007, pp. 167-211.
Singh, V. et al., "On the Thermal Elevation of a 60-Electrode Epiretinal Prosthesis for the Blind," IEEE Transactions on Biomedical Circuits and Systems, Dec. 2008, vol. 2, No. 4, pp. 289-300.
Singh, V. et al., "Specific Absorption Rate and Current Densities in the Human Eye and Head Induced by the Telemetry Link of a Dual-Unit Epiretinal Prosthesis," IEE Transactions on Antennas and Propagation, Oct. 2009, vol. 57, No. 10, pp. 3110-3118.
Sivaprakasam, M. et al., "Architecture Tradeoffs in High-Density Microstimulators for Retinal Prosthesis," IEEE Transactions on Circuits and Systems 14I: Regular Papers, Dec. 2005, vol. 52, No. 12, pp. 2629-2641.

Tokyo Institute of Technology: Yagi Laboratory webpage, "Visual Prosthesis (Retinal Implant & Biohybrid Retinal Implant)," (http://www.io.mei.titech.ac.jp/research/retina/index.html), printed Jun. 23, 2010, 5 pages.
Weiland, J.D et al., "Visual Prosthesis," Proceedings of the IEEE, Jul. 2008, vol. 96, No. 7, 9 pages.
Weiland, J.D. et al., "A Biomimetic Retinal Stimulating Array: Design Considerations," IEEE Engineering in Medicine and Biology Magazine, Sep./Oct. 2005, pp. 14-21.
Weiland, J.D. et al., "Retinal Prosthesis," Annu. Rev. Biomed. Eng., 2005, vol. 7, pp. 361-401, C-1-C-4.
Wu, L. et al., "An Efficient Wireless Power Link for High Voltage Retinal Implant," Proceedings of Biomedical Circuits and Systems Conference, 4 pages.
Xiao, X. et al., "In Vitro and In Vivo Evaluation of Ultrananocrystalline Diamond for Coating of Implantable Retinal Microchips," Journal of Biomedical Materials Research Part B: Applied Biomaterials, 2006, vol. 77, pp. 273-281.
Yanai, D. et al., Visual Performance Using a Retinal Prosthesis in Three Subjects with Retinitis Pigmentosa, American Journal of Ophthalmology, May 2007, vol. 143, No. 5, pp. 820-827.e2.
Yu, G. et al., "Large-Area, Full-Color Image Sensors Made with Semiconducting Polymers," Adv. Mater., vol. 10, No. 17, 1998, pp. 1431-1434.
Zhou, M. et al., "A Non-Coherent DPSK Data Receiver with Interference Cancellation for Dual-Band Transcutaneous Telemetries," IEEE Journal of Solid-State Circuits, Sep. 2008, vol. 43, No. 9, pp. 2003-2012.
An, K. H. et al., "Organic photodetector with spectral response tunable across the visible spectrum by means of internal optical microcavity," Organic Electronics, vol. 10, pp. 11520131157, (2009).
Bag, M. and Narayan, K. S., "Universality in the intensity-modulated photocurrent in bulk-heterojunction polymer solar cells," Phys. Rev. B., vol. 82, 075308, pp. 1-13, (2010).
Boyer, A. et al., "Colour Discrimination by Forward and Reverse Photocurrents in Bacteriorhodopsin-Based Photosensor," Biosensors and Bioelectronics, vol. 10, No. 5, pp. 415-422, (1995).
Boynton, R. M., "Rapid Chromatic Adaptation and the Sensitivity Functions of Human Color Vision," J. Opt. Soc. Am. 46, 172-179, (1956).
Butterwick, A. et al., "Effect of shape and coating of a subretinal prosthesis on its integration with the retina," Experimental Eye Research, vol. 88, pp. 22-29, (2009).
Chen, E-C. et al., "Polymer photodetector with voltage-adjustable photocurrent spectrum," Applied Physics Letters, vol. 96, pp. 043507-043507-3, (Jan. 29, 2010).
Chow, A. Y. et al. "The artificial silicon retina microchip for the treatment of vision loss from retinitis pigmentosa," Arch. Ophthalmol., vol. 122, No. 4, pp. 460-469 (Apr. 2004).
Clark, J. and Lanzani, G., "Organic photonics for communications," Nat Photon, vol. 4, pp. 438-446, (Jul. 2010).
Dacey, D. M., "Parallel pathways for spectral coding in primate retina," Annu. Rev. Neurosci., vol. 23, pp. 743-775, (2000).
Durban, M. M. et al., "Synthesis and Characterization of Thiophene-Containing Naphthalene Diimide n-Type Copolymers for OFET Applications," Macromolecules, vol. 43, No. 15, pp. 6348-6352, (2010).
Field, G. D. and Chichilnisky, E. J., "Information processing in the primate retina: Circuitry and coding," Annual Review of Neuroscience, vol. 30, p. 1-30, (Jul. 2007).
Forrest, S. R., "The path to ubiquitous and low-cost organic electronic appliances on plastic," Nature 428, pp. 911-918, (Apr. 29, 2004).
Gautam, V. et al., "Dynamics of Bulk Polymer Heterostructure/Electrolyte Devices," J. Phys. Chem. Lett. vol. 1, No. 22, pp. 3277-3282, (2010).
Gong, X. et al., "High-Detectivity Polymer Photodetectors with Spectral Response from 300 nm to 1450 nm," Science, vol. 325, No. 5948, pp. 1665-1667, (Aug. 13, 2009).
Gräber, P. and Trissl, H.-W., "On the rise time and polarity of the photovoltage generated by light gradients in chloroplast suspensions," FEBS Letters, vol. 123, No. 1, pp. 95-99, (Jan. 1981).

(56) References Cited

OTHER PUBLICATIONS

Halls, J. J. M. et al., "Efficient photodiodes from interpenetrating polymer networks," Nature 376, 498-500 (1995).

Humayun, M. S. et al., "Pattern electrical stimulation of the human retina," Vision Research, vol. 39, pp. 2569-2576, (1999).

Humayun, M. S. et al., "Visual perception in a blind subject with a chronic microelectronic retinal prosthesis," Vision Research, vol. 43, No. 24, pp. 2573-2581, (Nov. 2003).

Lörinczi, É. et al., "Voltage- and pH-Dependent Changes in Vectoriality of Photocurrents Mediated by Wild-type and Mutant Proteorhodopsins upon Expression in Xenopus Oocytes," J. of Mol. Bio., vol. 393, No. 2, pp. 320-341, (Oct. 23, 2009).

Macadam, D. L., "Chromatic Adaptation," J. Opt. Soc. Am, vol. 46, No. 7, pp. 500-513, (1956).

MRS Website : HH: Organic Photovoltaic Science and Technology, accessed at http://www.mrs.org/s_mrs/doc.asp?CID=25913&DID=307625, published on Apr. 5-9, 2010, p. 86.

Nassi, J. J. and Callaway, E. M., "Parallel processing strategies of the primate visual system," Nature Reviews Neuroscience, vol. 10, pp. 360-372, (May 2009).

Paillotin, G. et al., "Why does the light-gradient photovoltage from photosynthetic organelles show a wavelength-dependent polarity?," Biophys. J, vol. 65, No. 1, pp. 379-385, (Jul. 1993).

Punke, M. et al., "Dynamic characterization of organic bulk heterojunction photodetectors," Applied Physics Letters, vol. 91, Issue 7, pp. 071118-071118-3, (Aug. 2007).

Rizzo, J. F. et al., "Methods and perceptual thresholds for short-term electrical stimulation of human retina with microelectrode arrays," Invest. Ophthalmol. and Vis. Sci., vol. 44, No. 12, pp. 5355-5361, (Dec. 2003).

Schilinsky, P. et al., "Polymer photovoltaic detectors: progress and recent developments," Thin Solid Films, vols. 451-452, pp. 105-108, (Mar. 2004).

Schilinsky, P. et al., "Recombination and loss analysis in polythiophenebased bulk heterojunction photodetectors," Applied Physics Letters, vol. 81, Issue 20, pp. 3885-3887, (Nov. 2002).

Shoval, A. et al., "Carbon nanotube electrodes for effective interfacing with retinal tissue," Frontiers in Neuroengineering, vol. 2, No. 4, pp. 1-8, (2009).

Solomon, S. G. et al., "The machinery of colour vision," Nat. Rev. Neurosci., vol. 8, No. 4, pp. 276-286, (Apr. 2007).

Szendrei, K. et al., "Ambipolar all-polymer bulk heterojunction field-effect transistors," Journal of Materials Chemistry, vol. 20, pp. 1317-1321, (2010).

Wang, X. et al., "Integrated thin-film polymer/fullerene photodetectors for on-chip microfluidic chemiluminescence detection," Lab on a Chip, vol. 7, pp. 58-63, (2007).

Xu, T. et al., "Plasmonicnanoresona-tors for high-resolution colourfiltering and spectral imaging," Nat. Commun., vol. 1, Article 59, pp. 1-15, (2010).

Yan, H. et al. "A high-mobility electron-transporting polymer for printed transistors," Nature, vol. 457, pp. 679-686, (Feb. 5, 2009).

Notice of Allowance in U.S. Appl. No. 13/124,357 dtd Sep. 22, 2014 (7 pages).

Non-Final Office Action in U.S. Appl. No. 13/124,357 dtd Apr. 24, 2014 (10 pages).

European Search Report for European Application No. 10854014.7 mailed on Nov. 29, 2013.

Gautam, V., et al., "Single-Pixel, Single-Layer Polymer Device as a Tricolor Sensor with Signals Mimicking Natural Photoreceptors," (2011), Journal of the American Chemical Society, vol. 133, No. 44, pp. 17942-17949.

* cited by examiner

ARTIFICIAL RETINA DEVICE

CROSS-REFERENCE TO RELATED APPLICATIONS

The present application claims the benefit under 35 U.S.C. §371 of International Application Serial No. PCT/IB2012/053711, filed on Jul. 20, 2012, which claims the benefit of Indian Patent Application No. 2997/CHE/2011, filed on Aug. 30, 2011, the entire disclosures of each of which are incorporated herein by reference for any and all purposes in their entireties as if fully set forth herein.

BACKGROUND

The following description is provided to assist the understanding of the reader. None of the information provided or references cited is admitted to be prior art.

When light is received by a retina, complex signal processing takes place within the layers of the retina. Visual signals encode the information in the form of electrical "spikes." These electrical "spikes" are actually electro-chemical signals sent from ganglion cells to the visual cortex in the brain via the optic nerve. In some vision related diseases, the outer layers of the retina including the photoreceptors lose their function. However, the inner layers of the retina remain anatomically and functionally intact.

Advances have been made in the use of microphotodiode arrays and patterned stimulation electrodes as artificial retina devices. Such artificial retina devices are designed to address various vision related diseases such as retinal pigmentosa or macular degeneration or to augment normal vision. However, known artificial retina devices involve conventional electronics that are based on inorganic materials such as silicon or platinum/iridium oxide coated substrates. Such devices are not biocompatible or bio-stable and thus involve serious drawbacks to implantation in a human eye.

The drawbacks associated with traditional artificial retina devices are numerous. Such devices are known to cause serious gliosis in in-vivo cases as well as additional complications due to the mechanical incompatibility of the device with human tissue at the implant/tissue interface. In addition, such devices require bio-compatible electrodes in order to interface with human tissue and a video chip to process signals. Such devices further require an external power supply which may be provided via radio frequency signals or pulsed energy systems. In addition, traditional artificial retina devices have low visual acuity despite numerous advances in many areas (e.g., material, fabrication, energy supply, packaging, etc.). For example, traditional devices have allowed for a maximum of only 20/100 vision.

SUMMARY

The present technology provides an illustrative color-sensing device that includes an electrically-conductive substrate and a bulk heterojunction (BHJ) polymer layer formed on the electrically-conductive substrate. The color-sensing device is configured to detect a first color of two colors and produce a first electrical signal that includes a first current response indicating detection of the first color. The color-sensing device is further configured to detect a second color of the two colors and produce a second electrical signal that includes a second current response indicating detection of the second color.

In an embodiment, the illustrative color-sensing device further includes a Bragg reflector coupled to the substrate. In an embodiment, the Bragg reflector is coupled to a side of the substrate opposite the BHJ polymer layer, and the BHJ polymer layer is further configured to detect a third color and produce a third electrical signal that includes a current response indicating detection of the third color.

In an embodiment, the illustrative color-sensing device further includes an electrolyte or water layer formed on the BHJ polymer layer.

In an embodiment, the first current response includes a positive current spike in response to the detection of the first color, and the second current response includes a negative current spike in response to the detection of the second color.

The present technology further provides an illustrative method of sensing colors using a color-sensing device. The method includes receiving light at a bulk heterojunction (BHJ) polymer layer formed on a substrate. The color sensing device is configured to detect a first of two colors and produce a first electrical signal that includes a first current response indicating detection of the first color. The color sensing device is further configured to detect a second of the two colors and produce a second electrical signal that includes a second current response indicating detection of the second color. The method further includes detecting at least one of the two colors, and, in response to detecting the at least one of the two colors, conveying the first or second electrical signal.

In an embodiment, the electrolyte or water layer is formed on the BHJ polymer layer and includes an aqueous potassium chloride solution, sodium chloride solution, or de-ionized water.

In an embodiment, the first current response includes a positive current spike in response to the detection of the first color, and the second current response includes a negative current spike in response to the detection of the second color.

In an embodiment, the substrate includes an indium tin oxide coated glass and the BHJ polymer layer includes a regioregular alkylthiophene as a donor and N2200 as an acceptor.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
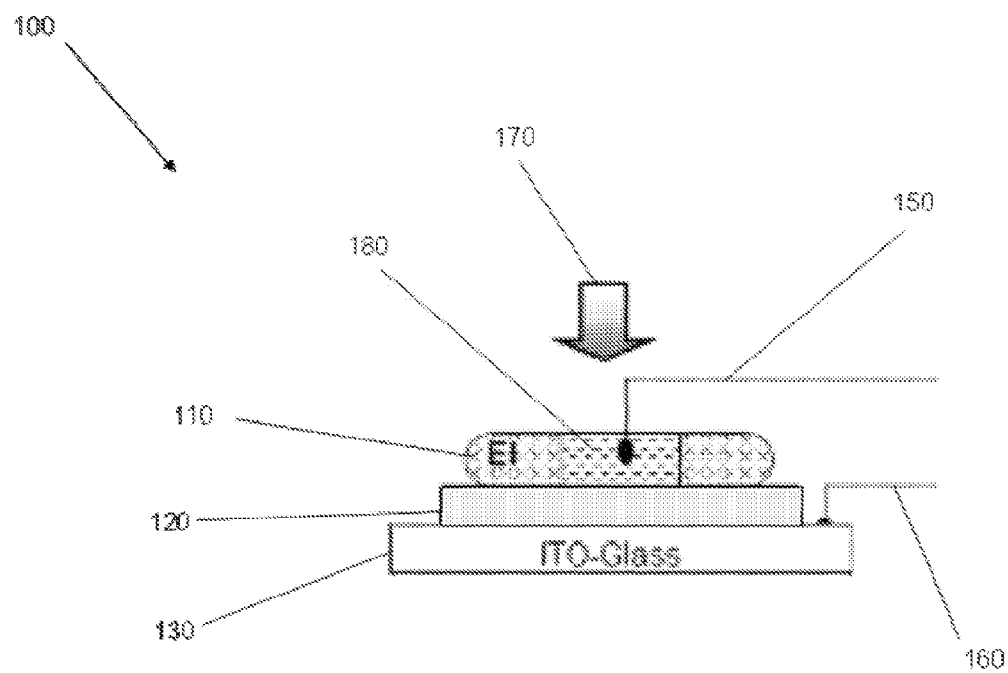
FIG. 1 depicts a cross-sectional view of a multicolor sensing pixel in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Traditional color sensing systems have generally involved two primary approaches: 1) combining three separate elements or sub-pixels each with photosensitivity tuned to a respective primary color; and 2) utilizing an array of color filters as a mask on a monochrome sensor. Such systems have several drawbacks including but not limited to the requirement of a large amount of post-acquisition image processing and the occurrence of undesirable artifacts in the image. Described herein are various systems and devices for providing a single pixel, single layer, and filter-free multicolor sensing technology that provides a characteristic polarity and temporal profile in response to receiving incident light of various respective wavelengths.

FIG. 1 depicts a cross-sectional view of a multicolor sensing pixel 100 in accordance with an illustrative embodiment. Multicolor sensing pixel 100 includes a substrate 130 having an electrically-conductive portion and a bulk heterojunction (BHJ) polymer layer 120 formed on and in physical contact with substrate 130. In an embodiment, substrate 130 is an electrically-conductive indium-tin-oxide (ITO) coated glass substrate. In an alternative embodiment, substrate 130 may include a transparent or semi-transparent electrically-conductive polymer such as poly(3,4-ethylenedioxythiophene): poly(4-styrene sulfonate) (PEDOT:PSS) which is formed on a substrate material such as glass, plastic, biocompatible composite, or any other substrate material known to those of skill in the art. In still another embodiment, substrate 130 may be a gold coated plastic substrate such as poly(ethylene terephthalate). In other embodiments, substrate 130 may comprise a first portion that includes a glass, plastic, biocompatible composites, or any other substrate material known to those of skill in the art capable of use in multicolor sensing pixel 100 and a second portion that includes any electrically-conductive material known to those of skill in the art capable of use in multicolor sensing pixel 100. In a further embodiment, substrate 130 is flexible, thus allowing for multicolor sensing pixel 100 to be securely and comfortably placed within the eye of a patient or included as part of an artificial retina device that may be placed within the eye of a patient.

In an embodiment, substrate 130 is connected in series to a current measuring device (or other device capable of receiving and analyzing the current response of BHJ polymer layer 120) by an electrical lead 160. In an embodiment, the current measuring device may be a current meter or oscilloscope that is configured to measure the current from electrical lead 160 in the form of a transient. In an alternative embodiment, electrical lead 160 may be connected to a counter ground electrode.

BHJ polymer layer 120 includes an interpenetrating network of electron donor and acceptor-type polymers such that photoexcitation of the polymer causes very fast charge transfer between the photoexcited donor and the acceptor. In an embodiment, BHJ polymer layer 120 includes a donor polymer of regioregular alkylthiophene (poly(3-alkylthiophene)) and an acceptor polymer belonging to the family of perylene and naphthalene derivatives such as N2200 (poly{[N,N'-bis (2-octyldodecyl)-naphthalene-1,4,5,8-bis(dicarboximide)-2, 6-diyl]-alt-5,5'-(2,2'-bithiophene)}) which is stable in aqueous media. In an alternative embodiment, the donor polymer may include poly-[3-octylthiophene] (P3OT) or any other suitable polymer known to those of skill in the art. In another embodiment, the donor polymer may include poly-[3-hexylthiophene] (PENT) and the acceptor polymer may include N2200. In an embodiment, the ratio of donor polymer to acceptor polymer is about 4:1. The thickness of BHJ polymer layer 120 is selected so that, in response to receiving light 170 at a first wavelength, an electrical signal is produced having a characteristic positive current spike and temporal profile, and, in response to receiving light 170 at a second wavelength, an electrical signal is produced having a characteristic negative current spike and temporal profile. As such, the current response of BHJ polymer layer 120 for various wavelengths of incident light will vary based on the thickness of BHJ polymer layer 120.

Multicolor sensing pixel 100 further includes a well 110 formed about an electrolyte or water 180 so as to hold electrolyte or water 180 in place and positioned adjacent to BHJ polymer layer 120. In an embodiment, well 110 may include a rubber, a silicone rubber (e.g., a polysiloxane composition such as polydimethylsiloxane (PDMS)), or any other material suitable for containing electrolyte or water 180 as known to those of skill in the art. In an embodiment, an electrical lead 150 is connected to electrolyte or water 180 and may be further connected to a counter electrode. Electrical lead 150 may be a copper wire, a gold wire, or any electrically-conductive lead known to those of skill in the art. The counter electrode may be electrical lead 150 itself and/or may include a fluorine doped tin oxide (FTO) glass, a copper electrode, a platinum electrode, or any other similar electrically-conductive electrode material known to those of skill in the art. In another embodiment, electrical lead 150 may be connected to a current measuring device, bipolar cell, or other device capable of receiving and analyzing the current response of BHJ polymer layer 120, and electrical lead 160 may be connected to the counter ground electrode. Electrolyte or water 180 functions as a layer between BHJ polymer layer 120 and the counter electrode and as a recipient of charge carriers from BHJ polymer layer 120. In an embodiment, electrolyte or water 180 may include a potassium chloride electrolyte solution, a sodium chloride aqueous solution, or de-ionized water. In alternative embodiments, electrolyte or water 180 may comprise another salt solution, a gel, or any other electrolyte known to those of skill in the art.

In an embodiment, multicolor sensing pixel 100 has a diameter of about 40 microns. In other embodiments, the diameter of multicolor sensing pixel 100 can range from about 10 microns to about 1000 microns or larger depending upon the desired spatial resolution of the incident colors. Smaller diameter pixels generally allow for higher spatial resolution of incident colors because additional pixels may be included in an array, thus allowing for the incident color to be independently analyzed at multiple locations.

The polar nature of the photocurrent response of multicolor sensing pixel 100 is a function of the differences in the rate of charge carrier accumulation at the BHJ polymer layer 120/electrolyte or water 180 interface and the BHJ polymer layer 120/electrically-conductive substrate 130 interface. For thick BHJ polymer layers (e.g., polymers having a thickness of greater than about 3-5 microns), photoexcitation of the BHJ polymer layer causes generation of charge carriers largely at the BHJ polymer layer 120/electrolyte or water 180 interface regardless of the wavelength of the incident light. Conversely, for thin film BHJ polymer layers (e.g., polymers having a thickness of less than about 200 nm-1 micron), photoexcitation of the BHJ polymer layer causes generation of charge carriers largely at the BHJ polymer layer 120/substrate 130 interface regardless of the wavelength of the incident light, resulting in a negative current spike. The accumulation of the charge carriers at the respective interfaces will in turn cause a voltage/current change between the electrode portions of substrate 130 and a ground. Where the generation of charge carriers occurs largely at the BHJ polymer layer 120/electrolyte or water 180 interface, a positive current spike is produced. Where the generation of charge carriers occurs largely at the BHJ polymer layer 120/substrate 130 interface, a negative current spike is produced. However, as discussed in more detail below, an appropriate "critical" thickness of BHJ polymer layer 120 may be chosen that provides distinctive photocurrent responses for incident light having a first wavelength and incident light having a second wavelength.

Accordingly, the voltage/current response of BHJ polymer layer 120 for various wavelengths of light will vary based on the thickness of BHJ polymer layer 120. In the embodiment of FIG. 1, an appropriate thickness of BHJ polymer layer 120 is chosen so as to provide sufficient two-color sensing capabilities so that received light having a first desired wavelength will produce a characteristic positive photocurrent spike while receive light having a second desired wavelength will produce a characteristic negative photocurrent spike. A BHJ polymer layer having such a thickness enables a wavelength dependent photocurrent ($I_{ph}$) response to incident light by virtue of the accumulation of charge carriers at the BHJ polymer layer 120/electrolyte or water 180 interface and the BHJ polymer layer 120/electrically-conductive substrate 130 interface. At such a thickness of BHJ polymer layer 120, charge carrier generation due to shorter wavelength incident light (e.g., blue/green light) occurs primarily at the BHJ polymer layer 120/electrolyte 180 interface and thus produces a positive photocurrent response spike, whereas charge carrier generation due to longer wavelength incident light (e.g., red light) occurs primarily at the BHJ polymer layer 120/substrate 130 interface and thus produces a negative photocurrent response spike.

For example, in an embodiment where the BHJ polymer layer includes a donor polymer of regioregular alkylthiophene and an acceptor polymer of stable N2200 and has a thickness of about 6 microns, an electrical signal having a positive photocurrent spike is produced in response to receiving light both at a wavelength of about 525 nanometers (nm) and at a wavelength of about 690 nm. When the thickness of such a BHJ polymer layer is changed to about 0.14 microns, an electrical signal having a negative current spike is produced in response to receiving light both at a wavelength of about 525 nm and at a wavelength of about 690 nm. However, when the thickness of such a BHJ polymer layer is changed to about 2 microns, an electrical signal having a positive current spike is produced in response to receiving light at a wavelength of about 525 nm while an electrical signal having a negative current spike was produced in response to receiving light at a wavelength of about 690 nm. In an embodiment, a BHJ polymer layer having a thickness of between about 1.8 microns and about 2.2 microns will provide the desired multicolor sensing capabilities. In alternative embodiments, the thickness of the BHJ polymer layer may be varied according to the ratio of the donor polymer to the acceptor polymer. According to such embodiments, a higher concentration of acceptor polymer within the BHJ polymer layer will allow for a smaller critical thickness of the BHJ polymer (i.e., a small thickness of the BHJ polymer layer that provides the desired multicolor sensing capabilities.

Figure 2:
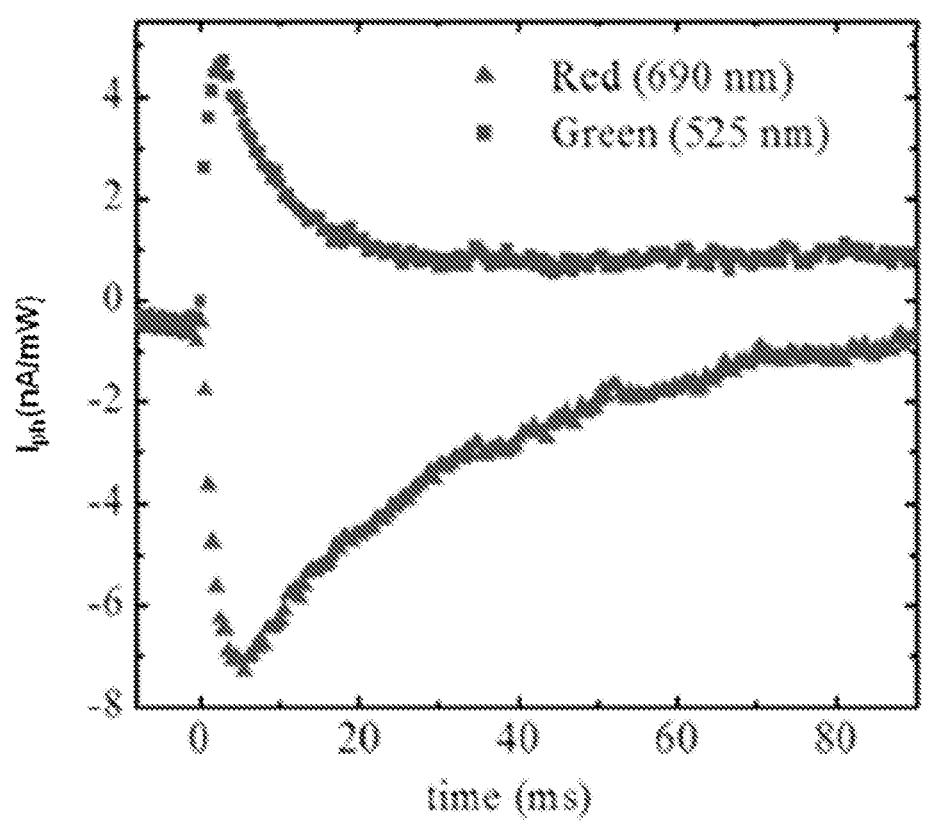
FIG. 2 depicts an output response from a multicolor sensing pixel including a BHJ polymer layer configured for two-color detection in accordance with an illustrative embodiment.

FIG. 2 depicts an output response from a multicolor sensing pixel including a BHJ polymer layer consisting of a donor polymer of regioregular alkylthiophene and an acceptor polymer of stable N2200 and having a thickness of about 2 microns in response to receiving light at wavelengths of 525 nm and 690 nm, respectively. As illustrated in FIG. 2, reception of light having a wavelength of about 525 nm produces a positive photocurrent spike, while reception of light having a wavelength of about 690 nm produces a negative photocurrent spike. Accordingly, such a BHJ polymer layer allows for detection of two opposing colors (i.e., blue/green light having a wavelength of about 525 nm and red light having a wavelength of about 690 nm) based on the output photocurrent polarity of the device.

In alternative embodiments, the BHJ polymer layer 120 may be chosen to produce desired photocurrent responses for any desired wavelengths of light (i.e., the device is not limited to the detection of blue/green and red light). Different wavelengths of light will exhibit distinct characteristics that will enable such wavelengths of light to be uniquely identified as discussed in more detail below.

In an embodiment, the multicolor sensing pixel may be utilized with an artificial retina device in the eye of a human or animal subject. The photocurrent responses generated by the multicolor sensing pixel resemble the response of retinal cone cells to reception of similar wavelength light. The change in potential/current between the electrically-conductive portions/electrodes of substrate 130 and electrolyte 180 is "sensed" by cells, for example neurons such as photoreceptor cells (e.g., rods, cones, etc.) associated with an eye of a patient in proximity to the artificial retina device. In alternative embodiments, the neurons are ganglion cells. Accordingly, the multicolor sensing pixel stimulates the bipolar cells associated with the eye or in proximity to the artificial retina device, thus providing an appropriate electrical signal to the bipolar cells based ultimately on the light received within BHJ polymer layer 120. As a result of the changes in potential within the multicolor sensing pixel in response to received incident light, the bipolar cells receive signals that mimic signal spikes/electrical response which would be received in a normal visual bipolar cell layer of the eye.

Figure 11:
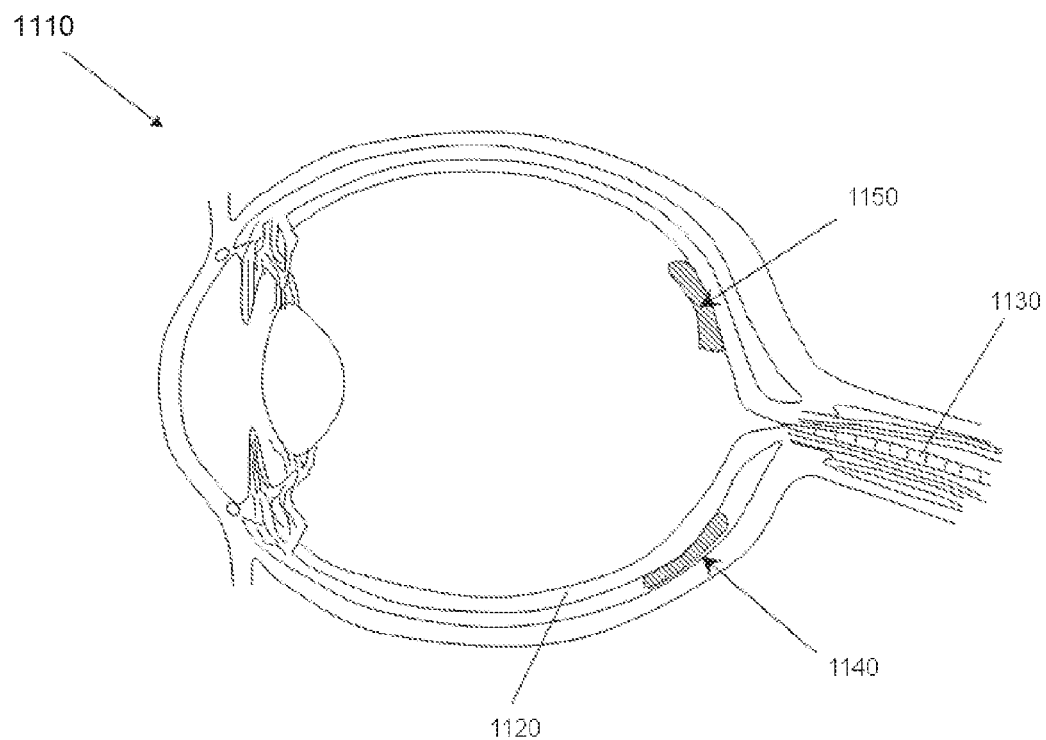
FIG. 11 is an illustration of representative sub-retinal and epi-retinal placements of artificial retina devices and within an eye of a patient in accordance with an illustrative embodiment.

FIG. 11 is an illustration of representative sub-retinal and epi-retinal placements of artificial retina devices 1140 and 1150 within an eye 1110 of a patient in accordance with an illustrative embodiment. In an embodiment, artificial retina devices 1140 and 1150 may include a multicolor sensing pixel 100 or 300 as described with respect to FIGS. 1 and 3. An illustrative sub-retinal placement of a device within an eye is illustrated by artificial retina device 1140 which is placed toward the back of eye 1110 behind retina 1120. An illustrative epi-retinal placement of a device within an eye is illustrated by artificial retina device 1150 which is placed toward the back of eye 1110 but in front of retina 1120. As such, electrodes of artificial retina device 1150 are in electrical contact with neurons such as photoreceptor cells or ganglion cells that communicate signals received from the electrodes to optical nerve 1130. In another embodiment, the electrodes of artificial retina device 1140 are placed in contact with bipolar cells of the eye. In an embodiment, artificial retina devices may be placed within the eye such that the substrates of the devices are in direct physical contact with the neurons, i.e., the ganglion cells or photoreceptor/bipolar cells.

In alternative embodiments, the multicolor sensing pixel may be utilized with devices other than that of an artificial retina device in order to discriminate between two or more colors and to generate an image. For example, a camera, sensor, or other imaging device known to those of skill in the art may utilize the multicolor sensing pixel to distinguish between incident lights having various wavelengths. In an embodiment, such an imaging device may not require color filters, subpixellation, or an external voltage bias. Such a device may include one or more electrodes configured to detect and distinguish the polarity of the electrical signals produced by the BHJ polymer layer in response to the reception of incident light. In an embodiment, the device may include a multi-electrode or multi-pixel array as discussed in more detail below with respect to FIG. 8a.

Such a device may further include a processor configured to receive and interpret the positive and negative current spikes in order to differentiate between the two or more colors. The processor may be further configured to interpret the output response from one or more multicolor sensing pixels and generate an image having color contrast based on the polarity and/or shape of the spikes of the electrical signals. Accordingly, different colors may be represented by unique temporal output signatures or mathematical functions and, upon identification of such signatures or mathematical functions, a representation of such colors and a corresponding image may be created. In an embodiment, the device may further comprise a display configured to display the generated image.

Figure 3:
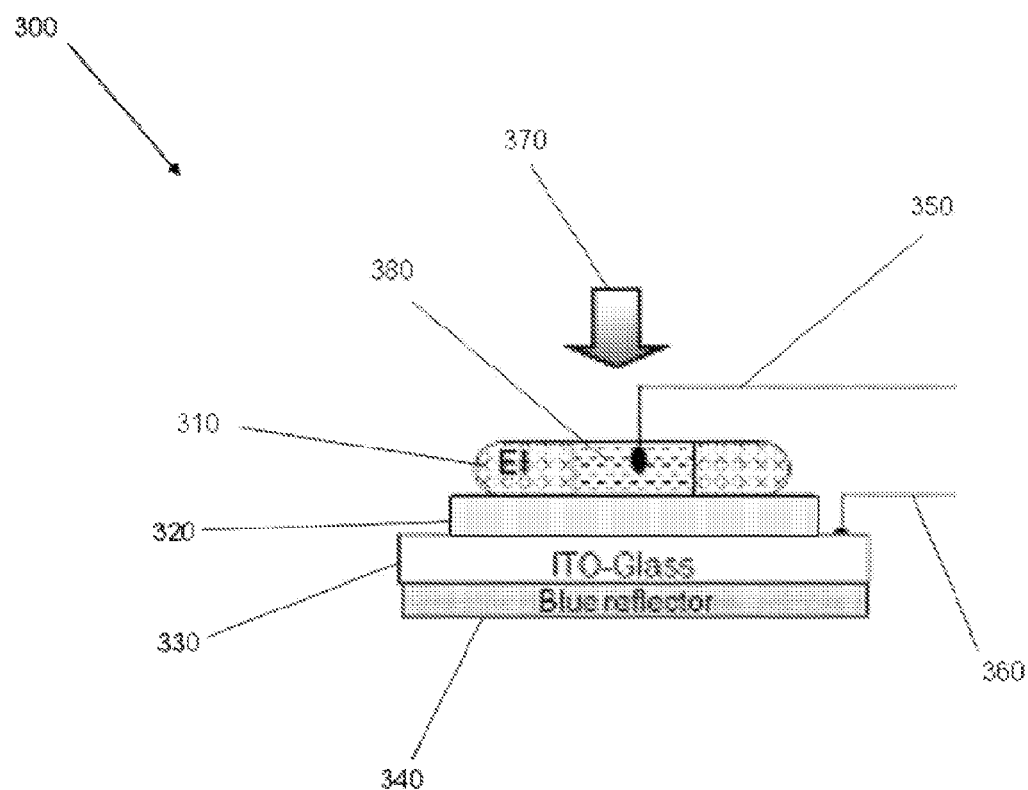
FIG. 3 depicts a cross-sectional view of a multicolor sensing pixel configured for three-color detection in accordance with an illustrative embodiment.

As illustrated in FIG. 2 above, the dynamics of the photocurrent response (e.g., rise and decay) for the two wavelengths of light are different. This difference in the dynamics of the photocurrent response combined with the use of a wavelength-selective substrate or reflector can be used to elicit a distinct response for incident light of a third wavelength to create a three-color detection device. FIG. 3 depicts a cross-sectional view of a multicolor sensing pixel 300 configured for three-color detection in accordance with an illustrative embodiment. According to such an embodiment, multicolor sensing pixel 300 may be configured to detect three distinct colors. Multicolor sensing pixel 300 includes similar elements as multicolor sensing pixel 100. For example, multicolor sensing pixel 300 includes a substrate 330 and a bulk heterojunction (BHJ) polymer layer 320 formed on substrate 330. An electrical lead 360 is connected to substrate 330. Multicolor sensing pixel 300 further includes a well 310 formed about an electrolyte or water 380 so as to hold electrolyte or water 380 in place and positioned adjacent to BHJ polymer layer 320. An electrical lead 350 may be connected to electrolyte or water 380 and may further be connected to a counter electrode. Electrolyte or water 380 functions as a layer between BHJ polymer layer 320 and the counter electrode and as a recipient of charges from BHJ polymer layer 320. In another embodiment, electrical lead 350 may be connected to a current measuring device, bipolar cell, or other device capable of receiving and analyzing the current response of BHJ polymer layer 320.

In addition to these elements, multicolor sensing pixel 300 also includes a Bragg reflector 340 configured to reflect a desired wavelength of light back to BHJ polymer layer 320. In alternative embodiments, substrate 330 may include a surface material with reflection characteristics biased toward the desired wavelength of light, and Bragg reflector 340 may be omitted. According to such an embodiment, the surface material includes a reflective coating that is based on a periodic layer system composed from two materials, one with a high index of refraction, e.g., zinc sulfide ($n=2.32$) or titanium dioxide ($n=2.4$), and one with a low index of refraction, e.g., magnesium fluoride ($n=1.38$) or silicon dioxide ($n=1.49$). This periodic system enhances the reflectivity of the surface over a given spectral band. The width of the spectral band over which the reflectivity is enhanced is determined by the ratio of the respective indices of refraction of the high index material and the low index material. Accordingly, the surface material can be designed as a long-pass filter, a short-pass filter, a bandpass filter, a notch filter, or a mirror with a specific reflectivity. In an alternative embodiment, a reflective paint as known to those of skill in the art may be used as the reflective surface material.

Figure 4:
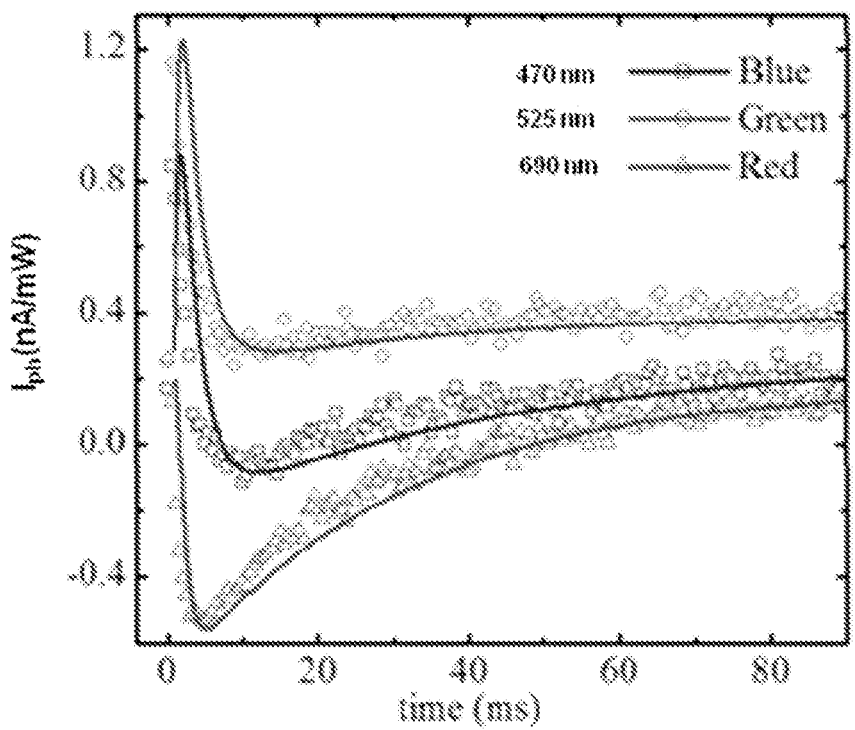
FIG. 4 depicts an output response from a multicolor sensing pixel configured for three-color detection in accordance with an illustrative embodiment.

In the embodiment of FIG. 3, Bragg reflector 340 is a blue reflector that is configured to reflect light at a wavelength of about 470 nm. In alternative embodiments, Bragg reflector 340 may be configured to reflect any desired wavelength of light back to BHJ polymer layer 320. In an embodiment, the presence of Bragg reflector 340 reflects light having a wavelength of about 470 nm toward BHJ polymer layer 320 where a distinctive photocurrent response is produced for such light. The photocurrent response for the blue light having a wavelength of about 470 nm may then be distinguished from the photocurrent responses of light having a wavelength of about 525 nm and light having a wavelength of about 690 nm. For example, the difference in the dynamics of the photocurrent response of the positive and negative signals produced by the 470 nm light incident on BHJ polymer layer 320 produces an initially positive photocurrent response followed by a negative photocurrent response, which can be distinguished from the respective positive and negative photocurrent responses of the 525 nm and 690 nm light. FIG. 4 depicts an output response from a multicolor sensing pixel configured for three-color detection (e.g., blue light at about 470 nm, green light at about 525 nm, and red light at about 690 nm) in accordance with an illustrative embodiment.

The photocurrent response for the respective wavelengths of the three-color detection scheme can be described algebraically as follows. The response for green light having a wavelength of about 525 nm can be expressed by the following equation:

$$I_{ph}=(1-e^{-t/\tau 1})e^{-t/\tau 2}. \qquad \text{Eqn. 1:}$$

The time constraints τ1 and τ2 characterize the rise and decay dynamics of the positive current response spike. The response for red light having a wavelength of about 690 nm can be expressed by the following equation:

$$I_{ph}=-(1-e^{-t/\tau 3})e^{-t/\tau 4}. \qquad \text{Eqn. 2:}$$

The time constraints τ3 and τ4 characterize the rise and decay dynamics of the negative current response spike. In the case of blue light having a wavelength of about 470 nm, the photocurrent response can be expressed by the summation of Equations 1 and 2 along with an additional pre-factor "a" and an offset "b":

$$I_{ph}=(1-e^{-t/\tau 1})e^{-t/\tau 2}-a(1-e^{-t/\tau 3})e^{-t/\tau 4}+b. \qquad \text{Eqn. 3:}$$

Example values for the respective parameters of these equations for the respective blue, green, and red incident lights are disclosed in the following table:

| Parameter | $\tau_1$ (ms) | $\tau_2$ (ms) | $\tau_3$ (ms) | $\tau_4$ (ms) | a | b |
|---|---|---|---|---|---|---|
| Blue | 0.8 | 2.5 | 1.0 | 45 | 0.25 | 0.14 |
| Green | 0.8 | 2.5 | 1.0 | 34 | 0.09 | 0.2 |
| Red | 0.8 | 1.0 | 1.0 | 30 | 0.9 | 0.18 |

The characteristic response for each of the desired wavelengths of light (i.e., 470 nm, 525, nm, and 690 nm) may thus be compared to the photocurrent response of incident light to determine the color/wavelength of the incident light using any algorithm or processing method known to those of skill in the art. In an embodiment, a comparator circuit using digital logic can be used to analyze the photocurrent response of the incident light.

Figure 5:
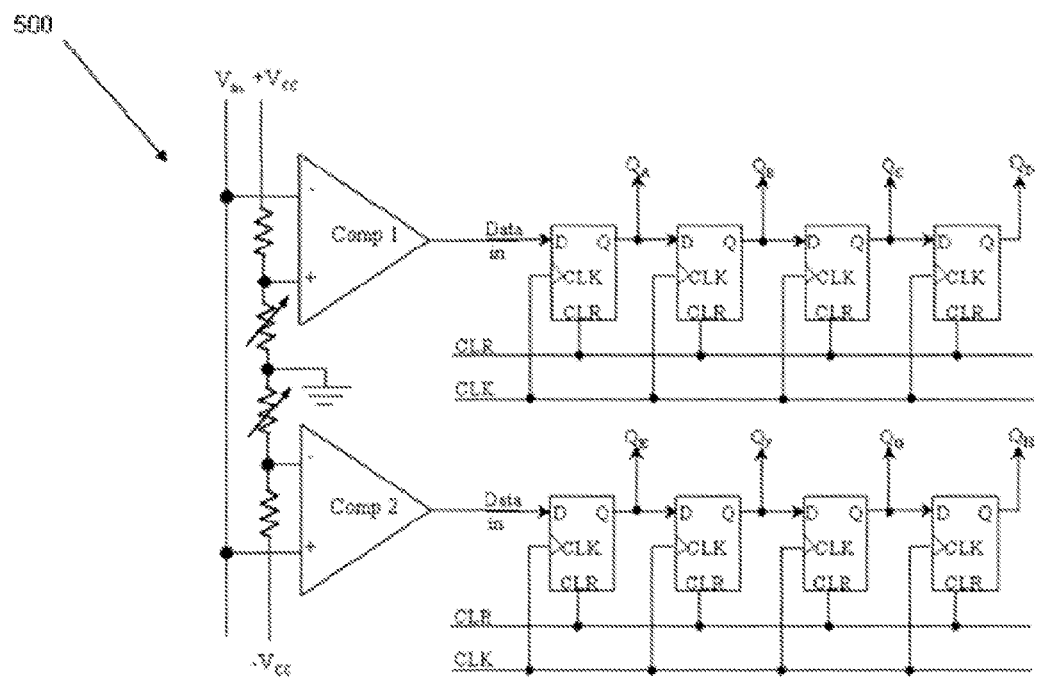
FIG. 5 depicts a comparator circuit for processing the photocurrent response of a multicolor sensing pixel receiving incident light in accordance with an illustrative embodiment.

FIG. 5 depicts a comparator circuit 500 for processing the photocurrent response of a multicolor sensing pixel receiving incident light in accordance with an illustrative embodiment. Comparator 1 of comparator circuit 500 is biased to detect a positive photocurrent response of the multicolor sensing pixel. Conversely, comparator 2 of the comparator circuit 500 is biased to detect a negative photocurrent response of the multicolor sensing pixel. The output of each comparator is connected to four-bit serial-in/parallel-out shift registers with appropriate clock pulses to digitize and store the data.

Figures 6, 7:
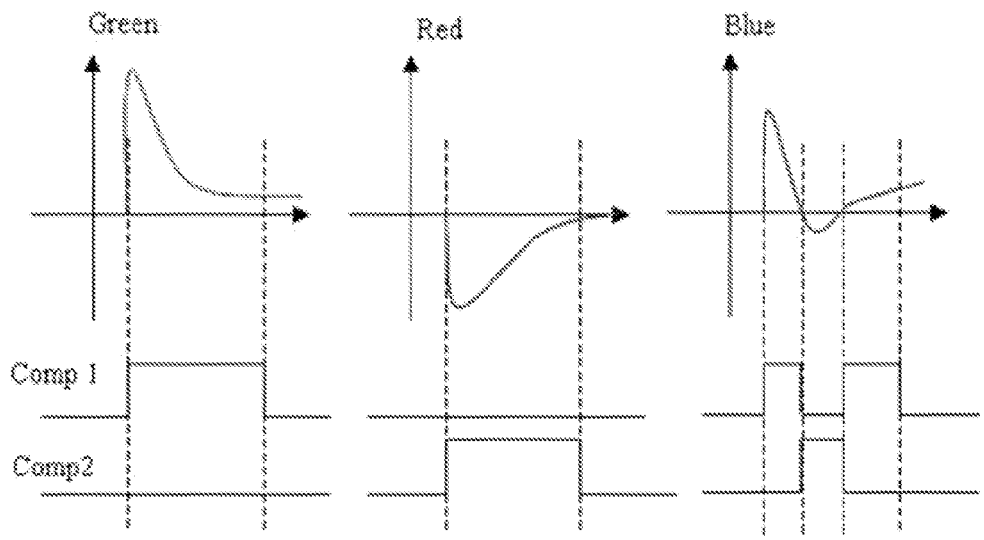
FIG. 6 depicts outputs of the comparators associated with respective photocurrent responses in accordance with an illustrative embodiment.
FIG. 7 depicts a possible output pattern of a comparator circuit using an eight-bit shift register in accordance with an illustrative embodiment.

FIG. 6 depicts outputs of the comparators associated with respective photocurrent responses in accordance with an illustrative embodiment. As mentioned above, comparator 1 is configured to detect a positive photocurrent response of the multicolor sensing pixel, while comparator 2 is configured to detect a negative photocurrent response of the multicolor sensing pixel. Accordingly, in an embodiment where the incident light has a wavelength of about 525 nm (i.e., green light), comparator 1 is "high" for all four clock pulses whereas comparator 2 is "low" for all four clock pulses. In an embodiment where the incident light has a wavelength of about 690 nm (i.e., red light), comparator 1 is "low" for all four clock pulses whereas comparator 2 is "high" for all four clock pulses. In an embodiment where the incident light has a wavelength of about 470 nm (i.e., blue light), both comparators 1 and 2 are "high" and "low" for various clock pulses.

In an embodiment, the bit pattern of the combined output could further be connected to an eight-bit parallel-in/serial-out shift register to provide the color information. According to such an embodiment, the respective outputs of comparator 1 and comparator 2 would be fed into the eight-bit parallel-in/serial-out register as inputs. The eight-bit parallel-in/serial-out register is configured to combine the two inputs and produce an eight-bit output based on corresponding clock pulses. As such, the output from the register could be increased to eight bits, thus increasing the accuracy of detection of the multiple colors. FIG. 7 depicts an example output pattern of a comparator circuit using an eight-bit shift register in accordance with an illustrative embodiment.

Figure 8A:
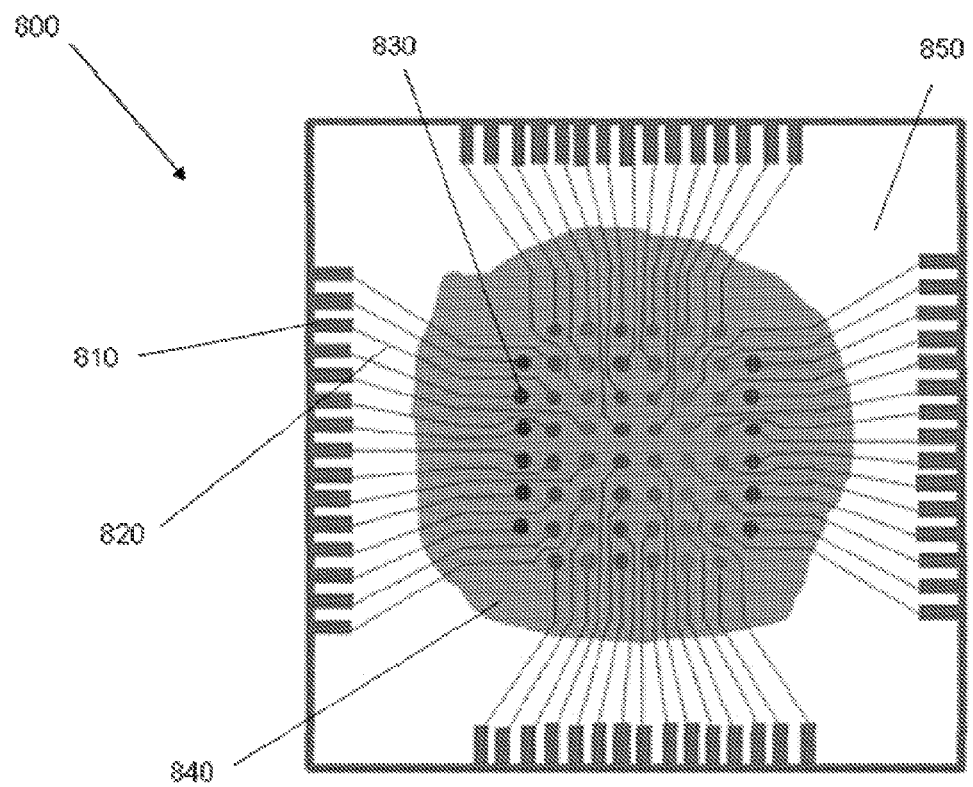
FIG. 8a depicts an 8×8 multi-electrode array in accordance with an illustrative embodiment.

FIG. 8a depicts an 8×8 multi-electrode array (MEA) 800 that utilizes the multicolor sensing pixel technology described above in accordance with an illustrative embodiment. The variation in pulse response parameters as a function of the wavelength of incident light over the entire visible range can be analyzed by dispersing white light across a patterned substrate such a MEA 800. MEA 800 includes a plurality of electrodes 830 arranged in an 8×8 matrix. In an embodiment, electrodes 830 include indium tin oxide (ITO). In alternative embodiments, electrodes 830 may include PEDOT, gold, or any other suitable electrically-conductive material known to those of skill in the art. In an embodiment, electrodes 830 have a diameter of about 40 microns and are spaced apart from other electrodes by about 200 microns. In another embodiment, the diameter of electrodes 830 can range from about 10 microns to about 1000 microns or larger depending upon the desired spatial resolution of the incident colors. Smaller diameter pixels/electrodes allow for higher spatial resolution of incident colors.

A BHJ polymer layer 840 is formed over electrodes 830 having an appropriate thickness to enable multicolor detection as discussed above. In an embodiment, BHJ polymer layer 840 has a thickness of between about 1.8 and about 2.2 microns. An electrolyte layer 850 is formed over BHJ polymer layer 840. In an embodiment, electrolyte layer 850 includes a 100 mM potassium chloride aqueous solution. In alternative embodiments, electrolyte layer 850 may include any other suitable electrolyte or de-ionized water.

Electrodes 830 are connected to electrical leads 820 which extend to contacts 810. Contacts 810 may in turn be connected to an amplifier and a current measuring device such as an oscilloscope for measuring the current responses generated at electrodes 830 in response to the reception of incident light at BHJ polymer layer 840.

Figure 8B:
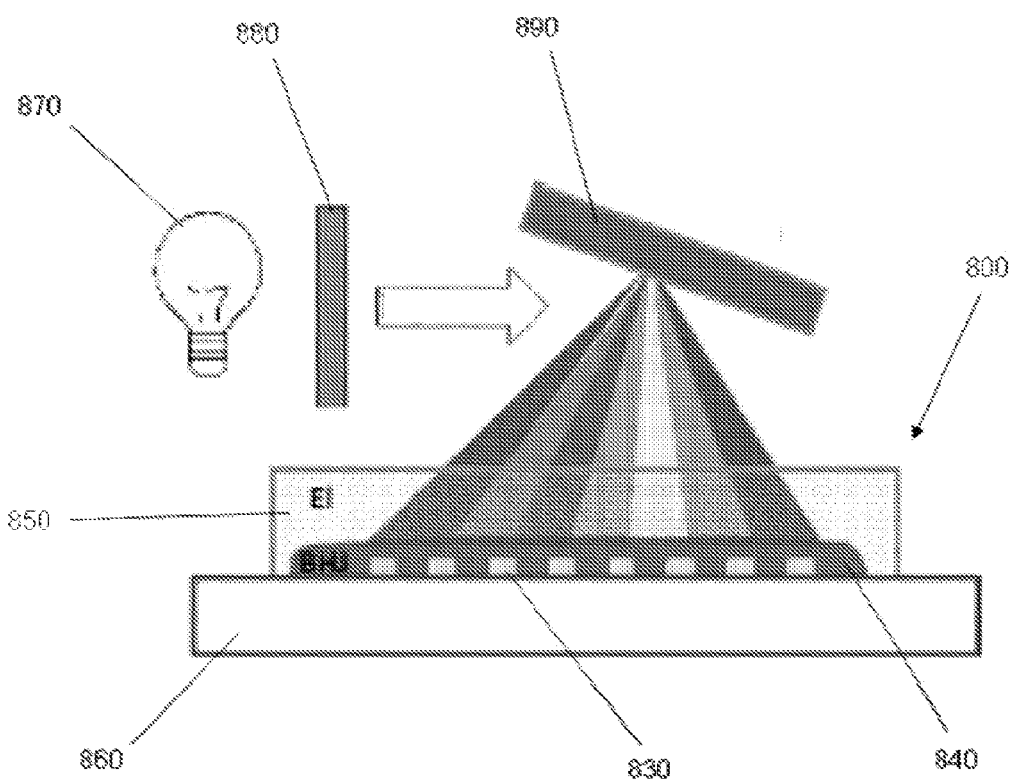
FIG. 8b depicts a system for focusing various wavelengths of the visible spectrum across a multi-electrode array in accordance with an illustrative embodiment.

FIG. 8b depicts a system for focusing various wavelengths of the visible spectrum across MEA 800 in accordance with an illustrative embodiment. The system includes a light source 870 configured to emit white light. In an embodiment, light source 870 is a light-emitting diode driven by a frequency generator. The system further includes a grating 890 configured to focus the light onto MEA 800 such that the visible spectrum is distributed uniformly across electrodes 830 of MEA 800. Electrodes 830 are formed on a substrate 860. A shutter 880 is configured to control the transmission of light to grating 890.

Figure 8C:
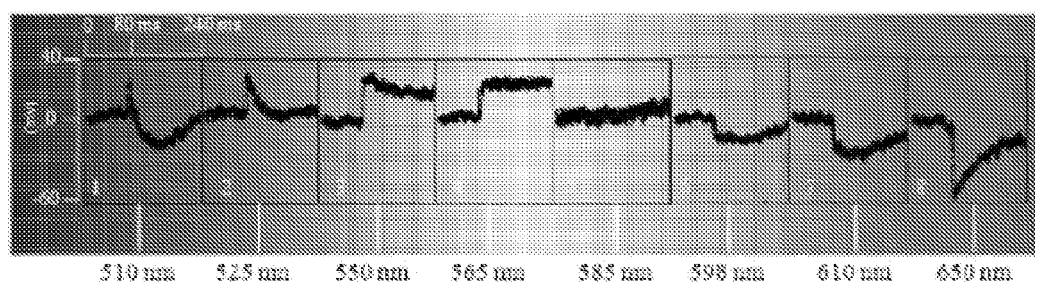
FIG. 8c depicts an output response from the multi-electrode array of FIGS. 8a and 8b in accordance with an illustrative embodiment.
Figure 8D:
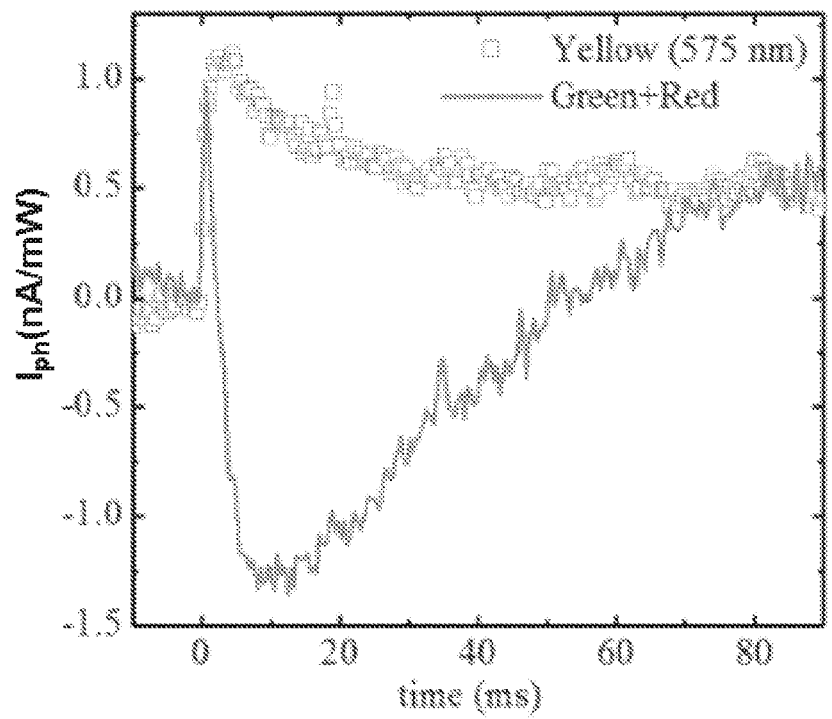
FIG. 8d depicts an output response for a wavelength of light associated with a pure yellow color and an output response for the wavelengths of light associated with the additive red and green colors in accordance with an illustrative embodiment.

FIG. 8c depicts an output response from the multi-electrode array of FIGS. 8a and 8b in accordance with an illustrative embodiment. FIG. 8c depicts the output response of electrodes 830 in response to reception of various wavelengths of incident light, e.g., 510 nm, 525 nm, 550 nm, 565 nm, 585 nm, 598 nm, 610 nm, and 650 nm. The output response was acquired by a LeCroy Waverunner 6100A oscilloscope at a sampling rate of 25 kilohertz using a 16-channel data acquisition card and MC-Rack software (available from MultiChannel Systems, Germany). As depicted in FIG. 8c, each wavelength of incident light generates a unique characteristic output response, thus allowing for the identification of the various wavelengths of lights/colors according to a received output response. The uniqueness of the output response for each wavelength of incident light further shows that a natural pure color can be distinguished from an additive color, i.e., the response to an incident pure-yellow light is different from a response to a yellow color obtained from a combination of red and green lights, because the output response for the wavelength of light associated with the pure color will be different from the combined output response of the wavelengths of light associated with the various additive colors. FIG. 8d depicts an output response for a wavelength of light associated with a pure yellow color and an output response for the wavelengths of light associated with the additive red and green colors in accordance with an illustrative embodiment. As indicated in FIG. 8d, the responses are distinct and unique.

Similarly, the output response of the multicolor sensing pixel/sensor may also convey information on the background (ambient) light and the background-bias introduced in a color, because the output response of the incident light will have a distinct polarity and shape for different background lights and background biases. For example, the color of an object under an incandescent bulb (which produces a yellowish-white light) may be distinguished from a compact fluorescent light source (which produces a bluish-white light), because of the difference the respective background lights will produce in the color signal of the object. The resulting differences in the color signal will generate distinct output responses from the multicolor sensing pixel/sensor that have unique polarities and/or shapes, thus enabling the background light/background biases to be distinguished.

Figure 9:
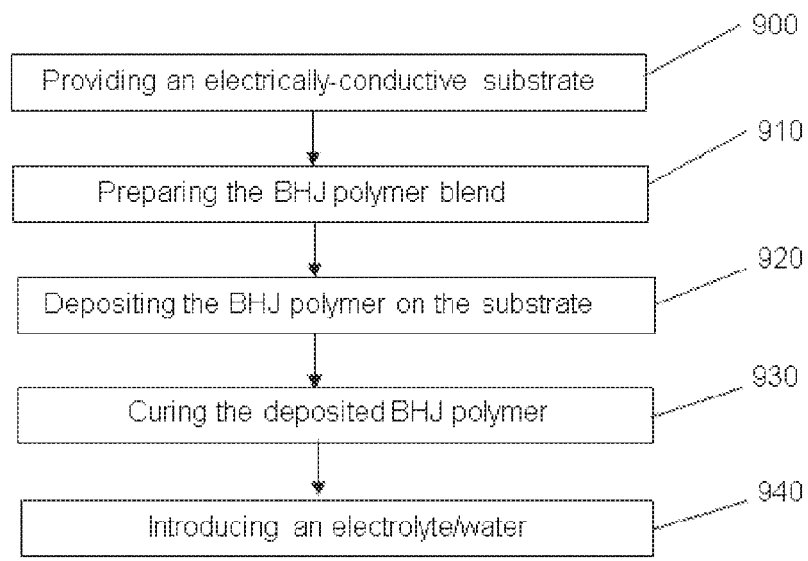
FIG. 9 depicts a method for producing a multicolor sensing pixel in accordance with an illustrative embodiment.

FIG. 9 depicts a method for producing a multicolor sensing pixel in accordance with an illustrative embodiment. In an operation 900, an electrically-conductive substrate is formed. In an embodiment, the electrically-conductive substrate includes an indium-tin oxide (ITO) glass substrate. In an alternative embodiment, a micro-electrode layer is formed on a non-conductive substrate and can be composed of electrically conducting polymer such as PEDOT:PSS.

In an operation 910, a bulk heterojunction (BHJ) polymer blend is formed by mixing a donor-type polymer with an acceptor-type polymer. In an embodiment, the donor-type polymer is poly-[3-octylthiophene] (P3OT) and the acceptor-type polymer is stable N2200 (poly{[N,N'-bis(2-octyldodecyl)-naphthalene-1,4,5,8-bis(dicarboximide)-2,6-diyl]-alt-5, 5'-(2,2'-bithiophene)}). According to such an embodiment, the blend of P3OT and N2200 is prepared in a 4:1 ratio with chlorobenzene as a solvent at a concentration of 20 mg/ml. In an alternative embodiment, the donor-type polymer may include regioregular alkylthiophene (poly(3-alkylthiophene)) or any other suitable polymer known to those of skill in the art and the acceptor-type polymer may include any suitable perylene or naphthalene diimides.

In an operation 920, the BHJ polymer blend is deposited on the electrically-conductive substrate to an appropriate thickness. In an embodiment, the BHJ polymer blend may be deposited by drop casting the BHJ polymer blend on the substrate. In an alternative embodiment, the BHJ polymer blend may be deposited by spin casting the BHJ polymer blend on the substrate or by any other process known to those of skill in the art. The thickness of the deposited BHJ polymer blend is selected so that, in response to receiving incident light at a first predetermined wavelength, an electrical signal is produced having a characteristic positive current spike and temporal profile, and, in response to receiving incident light at a second predetermined wavelength, an electrical signal is produced having a characteristic negative current spike and temporal profile.

In an operation 930, the deposited BHJ polymer blend is cured. In an embodiment, the BHJ polymer blend is cured by heating the blend to 80 degrees Celsius for approximately 20 minutes. In alternative embodiments, the BHJ polymer blend may be cured via other process or with different temperatures and curing times as known to those of skill in the art.

In an operation 940, an electrolyte or water layer is formed adjacent to the BHJ polymer blend to create an interface with the BHJ polymer blend. In an embodiment, the electrolyte is an aqueous potassium chloride solution with a concentration of 100 mM. In alternative embodiments, de-ionized water or any electrolyte known to those of skill in the art may be used.

In an embodiment, a well may be used to maintain the liquid electrolyte or water in contact with the BHJ polymer blend. The well may include material made from a rubber, a silicone rubber (e.g., a polysiloxane composition such as polydimethylsiloxane (PDMS)), or any other material suitable for containing electrolyte or water 180 as known to those of skill in the art. In an embodiment, the well may be a PDMS well with a diameter of about 1.5 mm. In other embodiments, the well may have a diameter of between about 0.5 mm and about 1000 mm according to the design needs of the multicolor sensing pixel. In an embodiment where the multicolor sensing pixel is used as part of an artificial retina device and placed within an eye, a well may not be required as the fluids present in the eye itself can act as the electrolyte. In other applications, the well may be fabricated on top of the BHJ polymer blend layer such that the electrolyte or water is in direct physical contact with the BHJ polymer blend layer.

In an embodiment, a counter electrode is placed in contact with the electrode or water layer. The counter electrode may include indium-tin oxide (ITO) glass, fluorine doped tin oxide (FTO) glass, or any other similar electrode material known to those of skill in the art.

Figure 10:
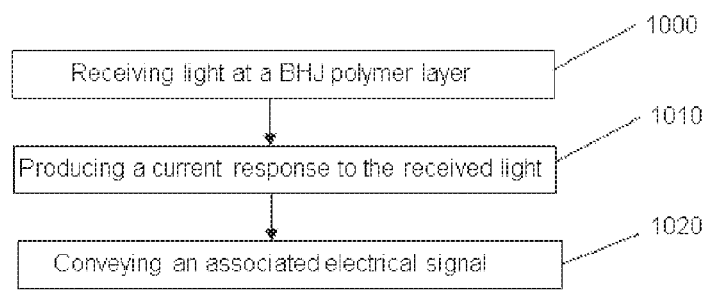
FIG. 10 depicts a method for detecting color using a multicolor sensing pixel in accordance with an illustrative embodiment.

FIG. 10 depicts a method for detecting color using a multicolor sensing pixel in accordance with an illustrative embodiment. In an operation 1000, incident light is received at a bulk heterojunction (BHJ) polymer layer of a multicolor sensing pixel. The BHJ polymer layer includes an interpenetrating network of electron donor and acceptor-type polymers such that photoexcitation of the polymer causes very fast charge transfer between the photoexcited donor and the acceptor. The thickness of the BHJ polymer layer is selected so that, in response to receiving incident light at a first wavelength, an electrical signal is produced having a characteristic positive current spike and temporal profile, and, in response to receiving incident light at a second wavelength, an electrical signal is produced having a characteristic negative current spike and temporal profile. As such, the current response of the BHJ polymer layer for various wavelengths of incident light will vary based on the thickness of the BHJ polymer layer.

In an operation 1010, a current response is produced by the multicolor sensing pixel corresponding to the wavelength of the incident light. In an embodiment, the current response includes a positive current spike in response to the detection of light of a first wavelength, and a negative current spike in response to the detection of light of a second wavelength.

In an operation 1020, an electrical signal associated with the current response produced by the multicolor sensing pixel is conveyed via electrical leads. In an embodiment, the electrical signal may be conveyed to cells within a human eye. In another embodiment, the electrical signal may be conveyed to analog or digital signal processing circuitry. For example, the electrical signal may be conveyed to a digital logic comparator circuit.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An apparatus for sensing multiple colors, the apparatus comprising:
    an electrically-conductive substrate; and
    a bulk heterojunction (BHJ) polymer layer formed on the electrically-conductive substrate, wherein the BHJ polymer layer is configured to:
        produce a first current response responsive to reception of a first color of two colors; and
        produce second current response responsive to reception of a second color of the two colors; and
    wherein the apparatus is configured to:
        produce a first electrical signal corresponding to the first current response indicating detection of the first color; and
        produce a second electrical signal corresponding to the second current response indicating detection of the second color; and
    wherein the electrically-conductive substrate comprises a Bragg reflector.

2. The apparatus of claim 1, wherein the electrically-conductive substrate comprises reflection characteristics configured to reflect a desired wavelength of light.

3. The apparatus of claim 2, wherein the Bragg reflector is coupled to a side of the electrically-conductive substrate opposite the BHJ polymer layer, and wherein the BHJ polymer layer is further configured to detect a third color and produce a third electrical signal comprising a current response indicating detection of the third color.

4. The apparatus of claim 1, further comprising an electrolyte or water layer formed on the BHJ polymer layer, wherein the electrolyte or water layer comprises an aqueous potassium chloride solution or de-ionized water.

5. The apparatus of claim 1, wherein the first current response comprises a positive current spike in response to the detection of the first color, and wherein the second current response comprises a negative current spike in response to the detection of the second color.

6. The apparatus of claim 1, wherein the electrically-conductive substrate comprises an indium tin oxide coated glass substrate, a gold coated plastic substrate, or an electrically-conductive polymer coated substrate.

7. The apparatus of claim 1, wherein the BHJ polymer layer comprises a regioregular alkylthiophene as a donor and perylene or naphthalene diimide as an acceptor.

8. The apparatus of claim 1, wherein the BHJ polymer layer is the only polymer layer on the color-sensing device.

9. The apparatus of claim 1, further comprising a plurality of pixels that each comprise the electrically-conductive substrate and the BHJ polymer layer.

10. The apparatus of claim 1, further comprising a comparator circuit configured to detect the first and second electrical signals and output a digital signal indicating detection of the corresponding first and second colors.

11. The apparatus of claim 1, wherein the electrically-conductive substrate is electrically coupled to a first electrical lead that is connected to a current measuring component.

12. The apparatus of claim 11, further comprising an electrolyte or water layer formed in a well on the BHJ polymer layer, wherein the electrolyte or water layer is electrically coupled to a second electrical lead that is connected to the current measuring component.

13. The apparatus of claim 1, wherein the BHJ polymer layer is the only polymer layer in a single pixel of the color-sensing device.

14. A method of multiple sensing colors using a color-sensing device, the method comprising:
  receiving light at a bulk heterojunction (BHJ) polymer layer formed on an electrically-conductive substrate;
  producing, by the BHJ polymer layer, a first current response to the received light, wherein the first current response is indicative of a first color, and wherein the BHJ polymer layer is configured to produce unique current responses for each of two colors;
  producing, by the BHJ polymer layer, a second current response to additional received light, wherein the second current response is indicative of a second color different from the first color; and
  in response to producing the first current response, conveying the first electrical signal indicating reception of light of the first color; and
  in response to producing the second current response, conveying the second electrical signal indicating reception of light of the second color.

15. The method of claim 14, wherein the electrically-conductive substrate comprises reflection characteristics configured to reflect a desired wavelength of light or a Bragg reflector configured to reflect the desired wavelength of light.

16. The method of claim 14 wherein an electrolyte or water layer is formed on the BHJ polymer layer, wherein the electrolyte or water layer comprises an aqueous potassium chloride solution or de-ionized water.

17. The method of claim 14, wherein the first current response comprises a positive current spike in response to the detection of the first color, and wherein the second current response comprises a negative current spike in response to the detection of the second color.

18. The method of claim 14, further comprising:
  conveying the at least one of the first electrical signal or the second electrical signal to a comparator circuit; and
  outputting a digital signal from the comparator circuit indicating detection of the corresponding first and second colors.

19. The method of claim 14, wherein the electrically-conductive substrate comprises an indium tin oxide coated glass, and wherein the BHJ polymer layer comprises a regioregular alkylthiophene as a donor and poly{[N,N'-bix(2-octyldodecyl)-naphthalene 1,4,5,8-bis(dicarboximide)-2,6-diyl]-alt-5,5'-(2,2'-bithiophene)} as an acceptor.

20. The method of claim 14, further comprising detecting a third color at the BHJ polymer layer and producing a third electrical signal comprising a current response indicating detection of the third color.

* * * * *

UNITED STATES PATENT AND TRADEMARK OFFICE
CERTIFICATE OF CORRECTION

| | |
|---|---|
| PATENT NO. | : 9,322,713 B2 |
| APPLICATION NO. | : 14/235603 |
| DATED | : April 26, 2016 |
| INVENTOR(S) | : Narayan et al. |

It is certified that error appears in the above-identified patent and that said Letters Patent is hereby corrected as shown below:

In the specification,

In Column 1, Line 7, delete "§371" and insert -- § 371 --, therefor.

In Column 4, Line 44, delete "(PENT)" and insert -- (PEHT) --, therefor.

Signed and Sealed this
Nineteenth Day of July, 2016

Michelle K. Lee
*Director of the United States Patent and Trademark Office*